United States Patent
Vallero

(10) Patent No.: US 8,660,652 B2
(45) Date of Patent: *Feb. 25, 2014

(54) TOPICAL ANALGESIA USING ELECTRICAL AND VIBRATION STIMULI

(75) Inventor: Rommel P. Vallero, Davis, CA (US)

(73) Assignee: Innova Medical Design LLC, Minneapolis, MN (US)

( * ) Notice: Subject to any disclaimer, the term of this patent is extended or adjusted under 35 U.S.C. 154(b) by 334 days.

This patent is subject to a terminal disclaimer.

(21) Appl. No.: 13/091,753

(22) Filed: Apr. 21, 2011

(65) Prior Publication Data

US 2011/0288456 A1    Nov. 24, 2011

Related U.S. Application Data

(60) Provisional application No. 61/327,491, filed on Apr. 23, 2010.

(51) Int. Cl.
*A61H 1/00* (2006.01)
*A61N 1/34* (2006.01)

(52) U.S. Cl.
USPC ............................................. 607/46; 601/46

(58) Field of Classification Search
USPC ................. 601/15, 17, 18, 21, 46; 607/46, 99
See application file for complete search history.

(56) References Cited

U.S. PATENT DOCUMENTS

| | | | |
|---|---|---|---|
| 2,258,857 A * | 10/1941 | McCann | 601/81 |
| 3,620,209 A | 11/1971 | Kravitz | |
| 4,550,733 A | 11/1985 | Liss et al. | |
| 4,924,880 A | 5/1990 | O'Neill et al. | |
| 5,366,489 A | 11/1994 | Burgio et al. | |
| 5,496,363 A | 3/1996 | Burgio et al. | |
| 7,686,773 B2 * | 3/2010 | Lindquist | 601/2 |
| 8,121,696 B2 * | 2/2012 | Vallero | 607/46 |
| 8,147,533 B2 * | 4/2012 | Baxter et al. | 607/108 |
| 2002/0013602 A1 * | 1/2002 | Huttner | 606/204 |
| 2004/0015188 A1 | 1/2004 | Coulter | |
| 2005/0149145 A1 | 7/2005 | Coulter | |
| 2009/0093761 A1 | 4/2009 | Sliwa et al. | |
| 2011/0022115 A1 * | 1/2011 | Salzhauer et al. | 607/46 |

FOREIGN PATENT DOCUMENTS

| | | |
|---|---|---|
| CA | 2243945 A1 | 6/1997 |
| WO | 0209575 | 2/2002 |
| WO | 2008094793 | 8/2008 |

OTHER PUBLICATIONS

International Search Report and Written Opinion issued in PCT/US2001/033468, mailed Jul. 20, 2011, 14 pages.
"3M Proposes Electronic Dental Anesthesia to Replace Conventional Anesthesia," www.3m.com/intl/FR/english/archive/story4971104.html, 1997, retrieved Feb. 22, 2013.

* cited by examiner

*Primary Examiner* — Kristen Matter
(74) *Attorney, Agent, or Firm* — Davis, Brown, Koehn, Shors & Roberts, P.C.; Sean D. Solberg

(57) ABSTRACT

Various embodiments disclosed herein relate to a device having a base and a stimulation module that can be attached to a patient's skin and actuated to mask the pain caused when sharp objects penetrate the skin. The stimulation module is designed to generate vibration energy, or alternatively, is designed to generate both vibration and electrical energy.

19 Claims, 3 Drawing Sheets

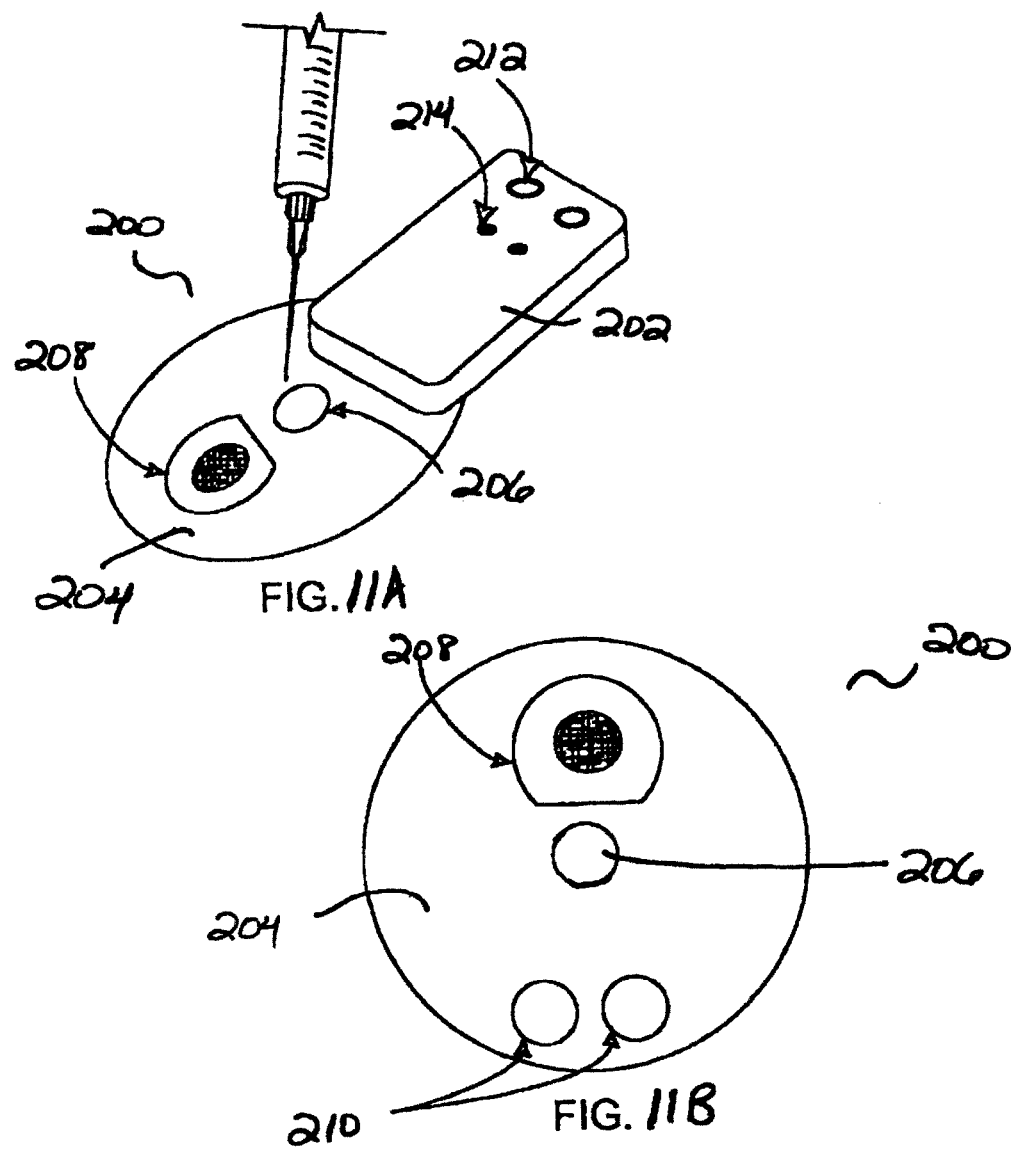

TOPICAL ANALGESIA USING ELECTRICAL AND VIBRATION STIMULI

CROSS-REFERENCE TO RELATED APPLICATIONS

This application claims the benefit under 35 U.S.C. §119 (e) to U.S. Provisional Patent Application No. 61/327,491, filed Apr. 23, 2010, entitled "Topical Analgesia Using Electrical and Vibration Stimuli," which is incorporated herein by reference in its entirety.

FIELD OF THE INVENTION

Various embodiments disclosed herein relate to methods and devices for reducing or eliminating the pain from injections and other similar procedures performed on skin by the application of transcutaneous electrical nerve stimulation ("TENS") and/or vibration stimulation. More specifically, the various embodiments relate to an adhesive skin patch and a coupleable stimulation unit used to deliver TENS or vibration or both to the patient.

BACKGROUND OF THE INVENTION

Injections and other procedures requiring the piercing of the skin have been a necessary part of medical treatment for humans and animals for centuries. Painful injections into and through the skin for immunizations, medication administration, blood sugar testing, phlebotomy, IV placement, and the like, are usually done without the use of a local or topical anesthetic. This results in an unpleasant experience for most adults, and may be an extremely traumatic event for children or other sensitive persons.

At times, the fear or aversion to these types of procedures may lead to noncompliance of treatments and testing by adults and children alike. Products to reduce the pain of injections and similar procedures do exist but have significant drawbacks and are not used often because of these limitations.

There is a need in the art for improved systems, methods, and devices for reducing or eliminating pain from injections and related procedures.

BRIEF SUMMARY OF THE INVENTION

Discussed herein are various embodiments relating to methods and devices for reducing or eliminating the pain from injections and other similar procedures performed on skin by the application of vibration stimulation, or alternatively by the application of a combination of electrical stimulation and vibration stimulation. More specifically, the various embodiments relate to an adhesive base and a coupleable stimulation module used to deliver vibration or both vibration and electrical stimulation to the patient.

In Example 1, an apparatus for providing topical analgesia during a procedure comprises a base, a vibration stimulation generating unit attachable to the base, and a flap hingedly coupled to the backing layer. The base has a backing layer, an adhesive layer positioned against the backing layer, and at least one access area defined by the base. The vibration stimulation generating unit is configured to transmit vibration energy to the base. The flap is configured to move between an open position and a closed position wherein the flap is disposed over the at least one access area.

Example 2 relates to the apparatus according to Example 1 and further comprising a controller operably coupled to the vibration stimulation generating unit, the controller configured to control the vibration stimulation generating unit.

Example 3 relates to the apparatus according to Example 2 and further comprising an input component operably coupled to the controller, the input component configured to allow a user to input a control signal to control intensity and duration of the vibration energy.

Example 4 relates to the apparatus according to Example 2, wherein the controller is further configured to initially gradually increase the vibration energy, generate randomly timed bursts of the vibration energy, automatically turn the apparatus on when the base and the vibration stimulation generating unit are coupled, and automatically shut off the apparatus when not in use.

Example 5 relates to the apparatus according to Example 1 and further comprising an attachment structure attachedly disposed between the vibration stimulation generating unit and the base, the attachment structure comprising one or more of ferromagnetic/electrically conductive discs, conductive buttons, conductive leads, conductive tabs, conductive hooks, conductive snaps, conductive adhesive, and hook and loop fastener, wherein the attachment structure is configured to allow transmission of vibration from the module to the base.

Example 6 relates to the apparatus according to Example 1, wherein the at least one access area is an orifice defined in the base, wherein the orifice has a circular, rectangular, or oval shape.

Example 7 relates to the apparatus according to Example 1, wherein the at least one access area is a notch.

Example 8 relates to the apparatus according to Example 1, wherein the at least one access area is an access area defined by an outer portion of the base.

Example 9 relates to the apparatus according to Example 1, wherein the vibration stimulation generating unit further comprises a display configured to display at least one of a status of the controller, battery status, operation of the vibration stimuli, and patient physiology.

Example 10 relates to the apparatus according to Example 1, wherein the vibration stimulation generating unit further comprises at least one of a light display and a sound generator, wherein the light display and the sound generator are configured to distract the patient during the procedure.

In Example 11, an apparatus for providing topical analgesia during a procedure comprises a base, a stimulation module attachable to the base, a controller operably coupled to the stimulation module, an input component operably coupled to the controller, and a flap hingedly coupled to the backing layer. The base, has a backing layer, an adhesive layer positioned against the backing layer, and at least one access area defined by the base. The stimulation module is configured to transmit energy to the base, wherein the stimulation module comprises a vibration stimulation generating unit configured to transmit vibration energy to the base. The controller is configured to control the stimulation module, and the input component is configured to allow a user to input a control signal to control intensity and duration of the energy transmitted to the base. The flap is configured to move between an open position and a closed position wherein the flap is disposed over the at least one access area.

Example 12 relates to the apparatus according to Example 11, wherein the stimulation module further comprises a display configured to display at least one of a status of the controller, battery status, operation of the stimulation module, and patient physiology.

Example 13 relates to the apparatus according to Example 11, wherein the stimulation module further comprises at least one of a light display and a sound generator, wherein the light display and the sound generator are configured to distract the patient during the procedure.

Example 14 relates to the apparatus according to Example 11, wherein the stimulation module further comprises an electrical stimulation generating unit configured to transmit electrical energy to the base, wherein the base further comprises an electrode.

In Example 15, an method for providing topical analgesia during a procedure comprises attaching a base to a patient's skin, attaching a module to the base, and generating, using the module, vibration energy in order to deliver a vibration stimuli through the electrode to the patient's skin to provide an analgesic effect. The base has at least one access area for allowing objects to pass through the at least one access area and into the patient's skin.

Example 16 relates to the apparatus according to Example 15 and further comprises the step of flipping down a flap hinged to the base over the at least one access point to act as a bandage dressing after the procedure is completed, wherein the base and flap remain on the patient to act as a bandage.

Example 17 relates to the apparatus according to Example 15 and further comprises the steps of inputting a control signal to the module to control the intensity and duration of the vibration energy, and controlling intensity and duration of the vibration energy using a controller in the module.

Example 18 relates to the apparatus according to Example 15 and further comprises the step of displaying on a display, at least one or more of the status of the controller, battery status, operation of the module and patient physiology.

Example 19 relates to the apparatus according to Example 15 and further comprises the step of generating one or more of a light display and sounds, for distracting the patient during the procedure.

Example 20 relates to the apparatus according to Example 15 further comprises generating, using the module, electrical energy in order to deliver an electrical stimuli through the base to the patient's skin to provide an analgesic effect, wherein the base comprises an electrode.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 11A is a perspective view of a device for reducing or eliminating the pain associated with an injection or other similar procedure, according to yet another embodiment.

FIG. 11B is a top view of the embodiment of FIG. 11A.

DETAILED DESCRIPTION OF THE INVENTION

Figure 1:
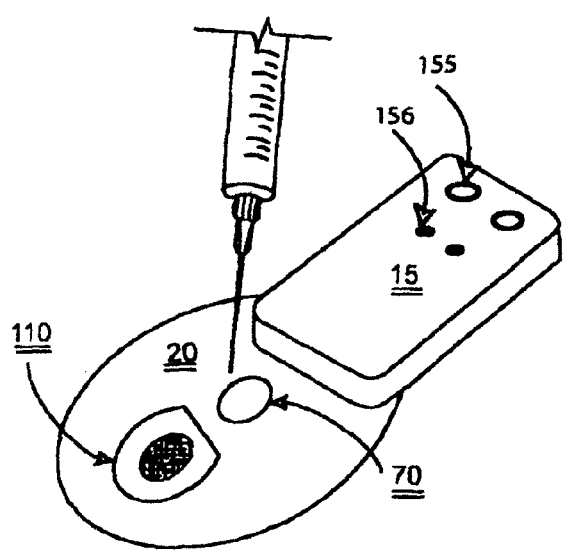
FIG. 1 is a perspective view of a device for reducing or eliminating the pain associated with an injection or other similar procedure, according to one embodiment.
Figure 2:
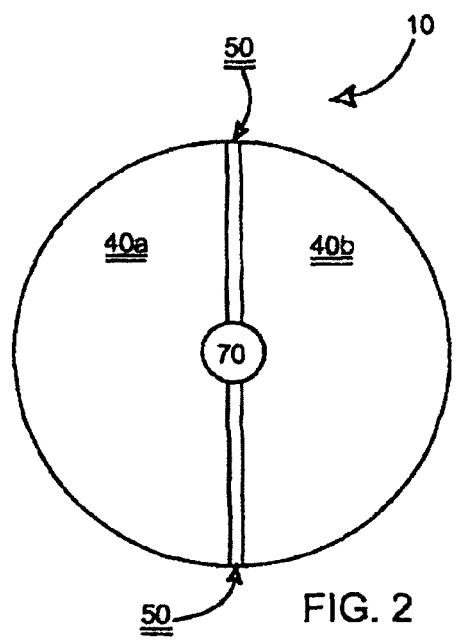
FIG. 2 is a bottom view of the embodiment of FIG. 1.
Figure 3:
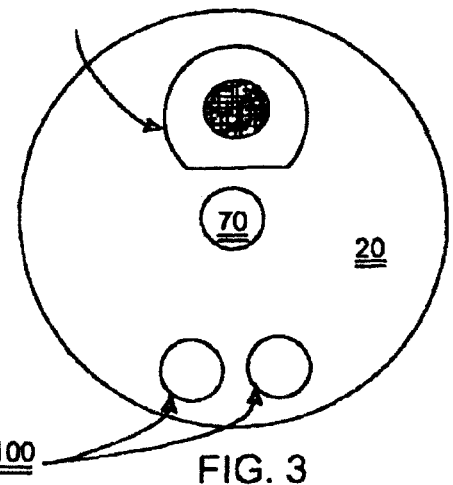
FIG. 3 is a top view of the embodiment of FIG. 1.
Figure 4:
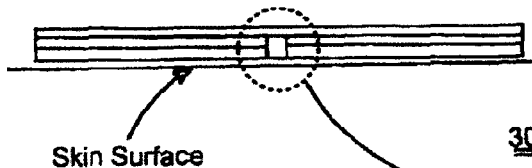
FIG. 4 is a side view of the embodiment of FIG. 1.
Figure 5:
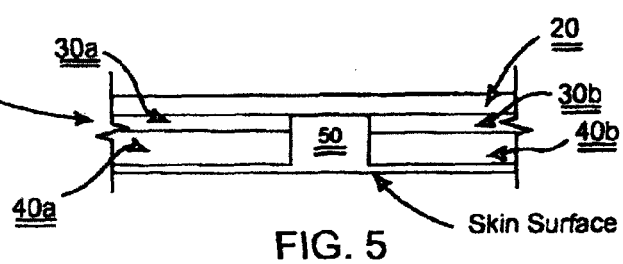
FIG. 5 is a magnified side view of the embodiment of FIG. 1.

Referring to FIGS. 1-5, one embodiment relates to an electrode 10 comprising a non-conductive flexible backing 20 with two electrically conductive surfaces 30a and 30b mounted onto this backing and positioned close to each other at roughly opposing ends of the electrode. Conductive skin adhesive 40a and 40b of the type commonly found on commercially available electrodes are positioned over each conductive surface. The conductive surfaces and the conductive adhesive overlying these surfaces are separated from each other by a small space 50 or a strip of non-conductive material so that the surfaces remain electrically insulated from one another.

Each conductive surface and their associated conductive adhesive may be electrically continuous with a means of connecting the electrode to the TENS/vibration unit 15. The method of connection may be via ferromagnetic/electrically conductive discs, conductive buttons, conductive snaps, conductive adhesive, hook and loop fastener, or other connective means 100 which may allow the transmission of both TENS and vibration stimulation to the electrode. Within or between the conductive surfaces is a window 70 or orifice large enough to allow needles and similar sharp instruments to pass through the electrode and into the skin layer underneath. The selection of materials may be similar to conventional electrodes and are well known to those skilled in the art of electrode construction.

Referring to FIG. 1, The TENS/vibration unit 15 is a separate electronic device, which is designed to attach to the electrode via various possible connective means, which may allow the transmission of both TENS and vibration stimulation to the electrode. Enclosed within the compact ergonomic casing is circuitry typical to that found in commercially available TENS generating units. This circuitry may have the ability to generate single or multiple frequency TENS stimuli and deliver this current to the electrode in parallel or in series. Variables such as frequency, current intensity, pulse width, and the like, may be made user adjustable.

Optionally included within the casing 15 is a means of creating the vibration stimuli. This may be accomplished by various means using rotational or oscillating vibration devices commonly found in cell phones and pagers, for example. One or more of these vibration devices may be placed in the unit depending on the application. Programmable micro controller circuitry similar to that found in many commercially available digital devices may also be enclosed within the unit to control the TENS and vibration stimuli. It may be pre-programmed to gradually increase both stimuli over a few seconds to a preset maximum level to prevent the initial sensation of surprise associated with a more sudden application of full electrical and TENS stimulation.

This micro controller may also be pre-programmed to deliver randomly timed bursts of electrical and/or vibration stimuli causing another form of distraction for the patient and making it more difficult to identify when the injection actually occurs. The micro controller may be programmed to deliver varying levels of TENS stimuli based on user input via small buttons 155 on the unit. For example, the user may be asked to press one button for low, medium or high intensity prior to application of the unit in order to deliver appropriate amounts of current to various age groups with differing sensitivity levels. Suitable membrane switches may be used to select the intensity and duration of electrical and vibration effect.

Alternately, wire, radio frequency (RF) or infrared control links may be used to provide a remote control so that the operator need not press directly onto the TENS/vibration unit. LEDs, or an LED display, video display or the like 156 may be used to indicate that the unit is operating, the batteries are charged or discharged, and also show the amount of electrical and vibration stimuli, and other data. This micro controller circuit may also be programmed to measure physiological variables via the electrode contacts such as resistance or capacitance of each individual's skin. These variables may be displayed on the display of the unit, or may be transmitted to other apparatus via data links (wired, RF, Infrared, or the like) so as to record patient data if required. Based on these brief initial readings, the micro controller may then deliver an appropriate amount of TENS or vibration stimulation.

The micro controller circuitry may also be used to identify different types of electrodes being used and then deliver a specific amount of stimuli based on that initial identification. For example, if the unit is connected onto a child type electrode, the unit may identify the specific electrode type via electrical or mechanical means unique to the electrode type and then deliver the correct amount of stimuli. The micro controller may also be pre-programmed so that the TENS and vibration stimuli begin once the unit is firmly attached to the electrode and stop when the unit is pulled away. This may eliminate the extra step of having to turn the unit on and off with every use. To power the entire unit, a small possibly rechargeable battery may also be enclosed within.

The embodiment described above is meant to reduce the pain experienced when needles and similar devices are inserted into skin. This unique electrode and TENS/vibration unit may be highly beneficial in alleviating pain due to immunizations, medication administration, phlebotomy, blood glucose checks, IV catheter placement, and the like. With minor changes in size and shape, this embodiment may be utilized for numerous other procedures as well.

In alternative embodiments, electrodes with the same basic features as described herein may be shaped and sized to fit over specific body structures such as earlobes and fingers. The access window size and or shape may also be designed to accommodate different uses. Because of this, other medical applications may also benefit from this device including painful skin treatments such as laser therapy, skin biopsy, wart removal, splinter and hook removal, or any potentially painful procedure done at or near the skin surface. Of course the veterinary field may also benefit from the topical analgesic effects found useful in human subjects. The use of this device is not limited to medical procedures. Painful cosmetic procedures such as ear and body piercing, tattooing, and hair removal may also be made more comfortable with various embodiments disclosed herein or similar thereto.

Commercially available electrodes have one conductive surface that may deliver only one circuit of electrical stimulation. Studies in the past have suggested that multiple specific electrical impulse frequencies may act to attenuate pain. See, e.g., Sluka K A, Walsh D., *Transcutaneous electrical nerve stimulation: basic science mechanisms and clinical effectiveness*, J Pain. 2003 April; 4(3): 109-21, incorporated herein by reference.

Figure 6:
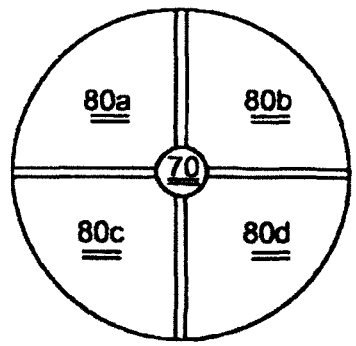
FIG. 6 is a bottom view of a device for reducing or eliminating the pain associated with an injection or other similar procedure, according to another embodiment.

Thus, it may be beneficial if a TENS electrode may deliver electrical stimulation of multiple different frequencies at the same time. Referring to FIG. 6, another embodiment may have four conductive surfaces on one electrode 80*a*, 80*b*, 80*c*, and 80*d* surrounding an access window 70 which may allow simplified, concentrated, simultaneous application of multiple frequency electrical stimulation. Electrical stimulation of differing frequencies may also be delivered via two isolated conductive surfaces as in FIG. 2 and FIGS. 7 through 10.

Figure 7:
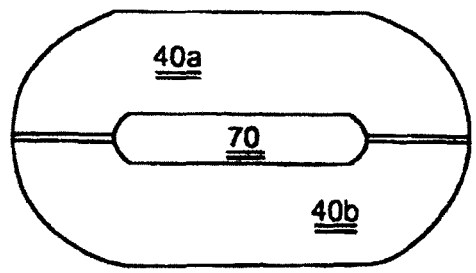
FIG. 7 is a bottom view of a device for reducing or eliminating the pain associated with an injection or other similar procedure, according to a further embodiment.

Referring now to FIG. 7, window 70 between the conductive surfaces 40*a* and 40*b* may also be in the shape of an elongated rectangle, oval, or other similar shape to allow TENS to be used as a topical analgesic for small laceration repairs or for IV catheter placement.

Figure 8:
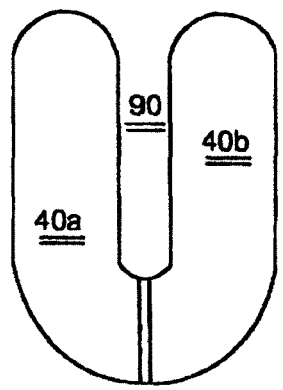
FIG. 8 is a bottom view of a device for reducing or eliminating the pain associated with an injection or other similar procedure, according to yet another embodiment.

Referring to FIG. 8, a notch 90, instead of a window may also be used to allow for more visualization of the skin area between conductive surfaces 40*a* and 40*b*.

Figure 9:
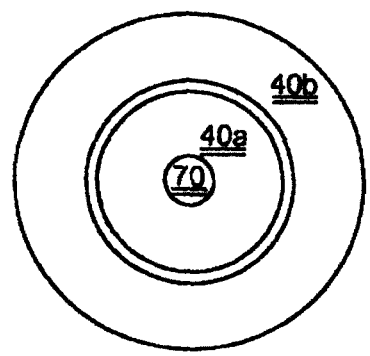
FIG. 9 is a bottom view of a device for reducing or eliminating the pain associated with an injection or other similar procedure, according to a further embodiment.
Figure 10:
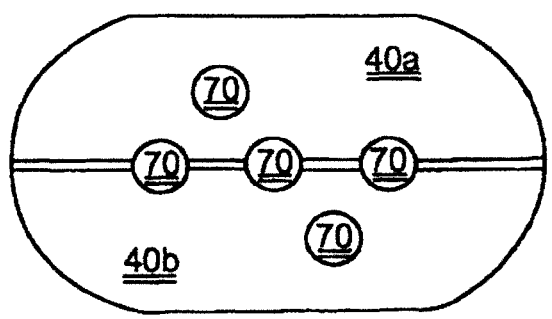
FIG. 10 is a bottom view of a device for reducing or eliminating the pain associated with an injection or other similar procedure, according to another embodiment.

Referring now to FIG. 9, the separate electrode conductive surfaces in the various embodiments contemplated herein may be arranged side by side as described above, in a concentric circular pattern around the access window 70, or any pattern that allows for the electrical isolation between the two conductive surfaces 40*a* and 40*b*. Referring to FIG. 10, the electrode may also be made with multiple windows 70 within or between the conductive surfaces 40*a* and 40*b* to allow for multiple injections such as those needed with immunizations or allergy testing.

Referring back to FIGS. 1 and 3, after a needle pierces the skin within the access window, an adhesive bandage flap with a gauze center 110 may be designed to flip down onto the skin within the window 70 to protect the site once the procedure is done. This may make it unnecessary to remove the electrode after a procedure in order to place a conventional bandage. The electrode serves as a bandage for the patient to help reduce bleeding, prevent infection, and aid in the healing process.

To help gain acceptance of the device by pediatric patients and to act as another form of visual distraction, the non-conductive backing of the electrode and/or the attached TENS/vibration unit may be printed with colors and/or shaped to resemble animals, cartoon characters, and the like. Small colorful LEDs or other light sources having low power drain may also be placed on the electrode and/or TENS/vibration unit to offer yet another interesting distraction. A flat panel display, for example, may provide information about the operation of the device and also generate a distracting pattern or image so the patient is distracted from the procedure.

Similarly, circuitry may be included within the electrode and/or the attached TENS/vibration unit to emit sounds, music, spoken words, and the like, meant to serve as an auditory distraction. Licensed characters may present audio messages, for example, to encourage and distract children during the procedure. After the procedure, the patient may be encouraged to keep the electrode as a type of reward or "sticker" for getting his/her "shots" that day, and the electrode may serve as bandage as well. Licensed characters or other designs may appear on the electrode and/or TENS/vibration unit for decorative or amusement purposes.

A smaller electrode similar to the embodiments described above may also be employed to provide nerve block to the fingers. The electrode may be wrapped around the base of a finger with the conductive surfaces overlying the nerves on either side of the finger. This placement may provide analgesia over an entire digit, resulting in decreased pain from blood sugar testing, laceration repairs, and other similar procedures. It is understood that the electrodes of the various embodiments disclosed herein may be made in other sizes and shapes without departing from the spirit and scope of the present invention, for other applications and operations.

Another embodiment of a device 200 for reducing or eliminating the pain from an injection or other similar procedure is depicted in FIGS. 11A and 11B. The device 200 has a base 200 (also referred to as a "patch") to which a stimulation unit 202 can be coupled. The base 200 has a first (or "top") layer 204, along with a second (or "bottom" or "underside") layer (not shown). According to one embodiment, the top layer 204 is a flexible layer that can also be referred to as a "backing" 204. The top layer can be made of flexible plastic, flexible cardboard, or any other known material commonly used in the backing of commercially available disposable bandages and similar medical products. The bottom layer, in one implementation, is an adhesive layer that can be placed in contact with a patient's skin to adhere the base 200 to the skin. The bottom layer can be made of any known material commonly used in the adhesive layer of commercially available disposable bandages and similar medical products.

In one embodiment, the base 200 is coupled to the stimulation unit 202 at the two connectors 210 on the base 200. Alternatively, the base 200 can have one connector, or more than two. It is understood that any known connector or coupling component can be used to coupled the stimulation unit 202 to the base 200 so long as the connector allows for transfer of the stimulation energy from the stimulation unit 202 to the base 200.

The base 200 also has an opening 206 defined in the base 200. The opening 206 as shown is an orifice 206 defined by the base 200. Alternatively, the opening 206 can take any shape in the base 200. Further, the opening 206 can be defined along an outer portion of the circumference of the base 200 such that the opening 206 is only partially defined by the base 200. It is further understood that the opening 206 can take any shape as contemplated above as depicted in FIGS. 7, 8, 9, and 10. It is understood that the opening 206 is large enough to allow needles and similar sharp instruments to pass through the base 200 and into the skin layer underneath.

According to various alternative embodiments, the base 200 can also have a cover or flap 208 that is hingedly coupled to the base 200 and positioned at or near the opening 206 such that the cover 208 can be moved between an open position and a closed position in which it covers the opening 206. According to one embodiment, the flap 208 has at least some adhesive on the surface that is configured to contact the base 200 in the closed position, thereby adhering the flap 208 to the base 200. In a further embodiment, the flap 208 can also have a gauze center. In one implementation, the closed position can protect the injection or insertion site once the procedure is done. In use, after a needle pierces the skin within the opening 206, the flap 208 can be flipped down onto the skin accessible through the opening 206 to protect the site once the procedure is done. This may make it unnecessary to remove the base 200 after a procedure in order to place a conventional bandage. The base 200 serves as a bandage for the patient to help reduce bleeding, prevent infection, and aid in the healing process.

According to one embodiment, the stimulation unit 202 is a separate device, which is designed to attach to the electrode via various possible connective means (as described above) and is configured to transmit either TENS or vibration stimulation or both to the base 200 and thus to the skin of the patient.

In accordance with one implementation, the stimulation unit 202 has a device configured to create the vibration stimuli. This may be accomplished by various devices or components using rotational or oscillating vibration devices commonly found in cell phones and pagers, for example. One or more of these vibration devices may be placed in the unit 202 depending on the application. Programmable micro controller circuitry similar to that found in many commercially available digital devices may also be enclosed within the unit to control the vibration stimuli. It may be pre-programmed to gradually increase the stimuli over a few seconds to a preset maximum level to prevent the initial sensation of surprise associated with a more sudden application of full vibration stimulation.

This micro controller, in one embodiment, may also be pre-programmed to deliver randomly timed bursts of vibration stimuli causing another form of distraction for the patient and making it more difficult to identify when the injection actually occurs. The micro controller may be programmed to deliver varying levels of vibration timuli based on user input via small buttons 212 on the unit. For example, the user can press one button for low, medium or high intensity prior to application of the unit in order to deliver appropriate amounts of vibration to various age groups with differing sensitivity levels. Suitable membrane switches may be used to select the intensity and duration of vibration effect.

Alternately, wire, radio frequency (RF) or infrared control links may be used to provide a remote control so that the operator need not press directly onto the vibration unit. LEDs, or an LED display, video display or the like 214 may be used to indicate that the unit is operating, the batteries are charged or discharged, and also show the amount of vibration stimuli, and other data.

The micro controller may also be pre-programmed so that the vibration stimuli begins once the unit 202 is firmly attached to the base 200 and stop when the unit 202 is pulled away. This may eliminate the extra step of having to turn the unit 202 on and off with every use. To power the entire unit 202, a small possibly rechargeable battery may also be enclosed within.

It is understood that, in the embodiments of the device shown in FIGS. 11A and 11B in which the stimulation device 202 transmits TENS (or both TENS and vibration), the base 200 is an electrode having any of the characteristics, structures, or features described with respect to the various other embodiments described above, and the stimulation unit 202 can have micro controller circuitry that is configured to control the TENS stimulation in the same fashion as described with respect to the various other embodiments described above.

The various embodiments described above relating to FIGS. 11A and 11B are meant to reduce the pain experienced when needles and similar devices are inserted into skin. These unique base and vibration unit implementations may be highly beneficial in alleviating pain due to immunizations, medication administration, phlebotomy, blood glucose checks, IV catheter placement, and the like. With minor changes in size and shape, these embodiments may be utilized for numerous other procedures as well.

Bases with the same basic features as described above may be shaped and sized to fit over specific body structures such as earlobes and fingers. The opening size and or shape may also be designed to accommodate different uses. Because of this, other medical applications may also benefit from this device including painful skin treatments such as laser therapy, skin biopsy, wart removal, splinter and hook removal, or any potentially painful procedure done at or near the skin surface. Of course the veterinary field may also benefit from the topical analgesic effects found useful in human subjects. The use of the various embodiments disclosed herein is not limited to medical procedures. Painful cosmetic procedures such as ear and body piercing, tattooing, and hair removal may also be made more comfortable with these devices and methods.

Like the other implementations described above, the backing of the base 200 and/or the attached stimulation unit 202 may be printed with colors and/or shaped to resemble animals, cartoon characters, and the like. Small colorful LEDs or other light sources having low power drain may also be placed on the base 200 and/or stimulation unit 202 to offer yet another interesting distraction. A flat panel display, for example, may provide information about the operation of the device and also generate a distracting pattern or image so the patient is distracted from the procedure.

Similarly, circuitry may be included within the base 200 and/or the attached stimulation unit 202 to emit sounds, music, spoken words, and the like, meant to serve as an auditory distraction. Licensed characters may present audio messages, for example, to encourage and distract children during the procedure. After the procedure, the patient may be encouraged to keep the base 200 as a type of reward or "sticker" for getting his/her "shots" that day, and the base 200 may serve as bandage as well. Licensed characters or other designs may appear on the base 200 and/or stimulation unit 202 for decorative or amusement purposes.

A smaller base similar to the invention described above may also be employed to provide nerve block to the fingers. The base may be wrapped around the base of a finger. This placement may provide analgesia over an entire digit, resulting in decreased pain from blood sugar testing, laceration repairs, and other similar procedures. It is understood that the various embodiments of the base disclosed herein may be made in other sizes and shapes without departing from the spirit and scope of the present invention, for other applications and operations.

Although the present invention has been described with reference to preferred embodiments, persons skilled in the art will recognize that changes may be made in form and detail without departing from the spirit and scope of the invention.

What is claimed is:

1. An apparatus for providing topical analgesia during a procedure, comprising:
    (a) a base comprising:
        (i) a backing layer;
        (ii) an adhesive layer positioned against the backing layer, the adhesive layer being configured to be adherable to a patient's skin; and
        (iii) at least one access area defined by the base, the at least one access area configured to allow objects to pass through the access area and into the patient's skin;
    (b) a vibration stimulation generating unit attachable to the base, the vibration stimulation generating unit configured to transmit vibration energy to the base; and
    (c) a flap hingedly coupled to the backing layer, the flap configured to move between an open position and a closed position wherein the flap is disposed over the at least one access area.

2. The apparatus of claim 1, further comprising a controller operably coupled to the vibration stimulation generating unit, the controller configured to control the vibration stimulation generating unit.

3. The apparatus of claim 2, further comprising an input component operably coupled to the controller, the input component configured to allow a user to input a control signal to control intensity and duration of the vibration energy.

4. The apparatus of claim 2, wherein the controller is further configured to initially gradually increase the vibration energy, generate randomly timed bursts of the vibration energy, automatically turn the apparatus on when the base and the vibration stimulation generating unit are coupled, and automatically shut off the apparatus when not in use.

5. The apparatus of claim 1, further comprising an attachment structure attachedly disposed between the vibration stimulation generating unit and the base, the attachment structure comprising one or more of ferromagnetic/electrically conductive discs, conductive buttons, conductive leads, conductive tabs, conductive hooks, conductive snaps, conductive adhesive, and hook and loop fastener, wherein the attachment structure is configured to allow transmission of vibration from the module to the base.

6. The apparatus of claim 1, wherein the at least one access area is an orifice defined in the base, wherein the orifice has a circular, rectangular, or oval shape.

7. The apparatus of claim 1, wherein the at least one access area is a notch.

8. The apparatus of claim 1, wherein the at least one access area is an access area defined by an outer portion of the base.

9. The apparatus of claim 1, wherein the vibration stimulation generating unit further comprises a display configured to display at least one of a status of the controller, battery status, operation of the vibration stimuli, and patient physiology.

10. The apparatus of claim 1, wherein the vibration stimulation generating unit further comprises at least one of a light display and a sound generator, wherein the light display and the sound generator are configured to distract the patient during the procedure.

11. An apparatus for providing topical analgesia during a procedure, comprising:
    (a) a base comprising:
        (i) a backing layer;
        (ii) an adhesive layer positioned against the backing layer, the adhesive layer being configured to be adherable to a patient's skin; and
        (iii) at least one access area defined by the base, the at least one access area configured to allow objects to pass through the access area and into the patient's skin;
    (b) a stimulation module attachable to the base, the stimulation module configured to transmit energy to the base, wherein the stimulation module comprises a vibration stimulation generating unit configured to transmit vibration energy to the base;
    (c) a controller operably coupled to the stimulation module, the controller configured to control the stimulation module;
    (d) an input component operably coupled to the controller, the input component configured to allow a user to input a control signal to control intensity and duration of the energy transmitted to the base; and
    (e) a flap hingedly coupled to the backing layer, the flap configured to move between an open position and a closed position wherein the flap is disposed over the at least one access area.

12. The apparatus of claim 11, wherein the stimulation module further comprises a display configured to display at least one of a status of the controller, battery status, operation of the stimulation module, and patient physiology.

13. The apparatus of claim 11, wherein the stimulation module further comprises at least one of a light display and a sound generator, wherein the light display and the sound generator are configured to distract the patient during the procedure.

14. The apparatus of claim 11, wherein the stimulation module further comprises an electrical stimulation generating unit configured to transmit electrical energy to the base, wherein the base further comprises an electrode.

15. A method for providing topical analgesia during a procedure, comprising:
   attaching a base to a patient's skin, the base having at least one access area for allowing objects to pass through the at least one access area and into the patient's skin;
   attaching a module to the base;
   generating, using the module, vibration energy in order to deliver a vibration stimuli through an electrode to the patient's skin to provide an analgesic effect; and
   flipping down a flap hinged to the base over the at least one access area to act as a bandage dressing after the procedure is completed, wherein the base and the flap remain on the patient to act as a bandage.

16. The method of claim 15 further comprising the steps of:
   inputting a control signal to the module to control the intensity and duration of the vibration energy; and
   controlling intensity and duration of the vibration energy using a controller in the module.

17. The method of claim 15, further comprising the step of displaying on a display, at least one or more of the status of the controller, battery status, operation of the module and patient physiology.

18. The method of claim 15, further comprising the step of generating one or more of a light display and sounds, for distracting the patient during the procedure.

19. The method of claim 15, further comprising generating, using the module, electrical energy in order to deliver an electrical stimuli through the base to the patient's skin to provide an analgesic effect, wherein the base comprises an electrode.

* * * * *